United States Patent [19]

Grahn et al.

[11] Patent Number: 5,322,686
[45] Date of Patent: Jun. 21, 1994

[54] PHARMACEUTICAL PREPARATION FOR CONTROLLING PATHOGENIC INTESTINAL BACTERIA

[76] Inventors: Eva E. Grahn, Bondegatan 32, Umeå S-902 54; Stig E. F. Holm, Gimonäsvägen 25, Umeå S-902 40, both of Sweden

[21] Appl. No.: 861,796
[22] PCT Filed: Dec. 19, 1990
[86] PCT No.: PCT/SE90/00850
§ 371 Date: Jun. 16, 1992
§ 102(e) Date: Jun. 16, 1992
[87] PCT Pub. No.: WO91/09608
PCT Pub. Date: Jul. 11, 1991

[30] Foreign Application Priority Data
Dec. 22, 1989 [SE] Sweden .................. 8904332

[51] Int. Cl.⁵ .............................. C12N 1/20
[52] U.S. Cl. ...................... 424/93 H; 424/93 J; 435/253.4; 435/885
[58] Field of Search ............... 424/93 H, 93 J; 435/253.4, 885

[56] References Cited

U.S. PATENT DOCUMENTS 5,143,845  9/1992  Masuda .................... 435/253.4

FOREIGN PATENT DOCUMENTS 62-201823  9/1987  Japan.
1-066124   3/1989  Japan.
1333709    8/1987  U.S.S.R.
1423586    9/1988  U.S.S.R.
1190386    5/1970  United Kingdom.

Primary Examiner—Douglas W. Robinson
Assistant Examiner—Jean C. Witz
Attorney, Agent, or Firm—Merchant, Gould, Smith, Edell, Welter & Schmidt

[57] ABSTRACT

A pharmaceutical preparation for controlling pathogenic microorganisms causing diarrhoea and other gastrointestinal troubles in man and in animals contains *Streptococcus lactis* strain LIa in at least one pharmaceutically acceptable carrier medium in which the microorganism retains its viability. The use of the preparation for controlling pathogenic microorganisms causing diarrhoea and other gastrointestinal infections in man and in animals is also described.

9 Claims, No Drawings

PHARMACEUTICAL PREPARATION FOR CONTROLLING PATHOGENIC INTESTINAL BACTERIA

The present invention relates to a pharmaceutical preparation for controlling pathogenic intestinal bacteria in man and in animals, with a view to preventing and/or treating diarrhoea and other gastrointestinal troubles.

BACKGROUND OF THE INVENTION

Diarrhoea and other gastrointestinal troubles caused by pathogenic microorganisms constitute a widespread health problem, which affects in particular tourists travelling abroad, people having received cancer therapy involving antibiotics or radiation, and people working in day nurseries. Such pathogenic intestinal bacteria causing diarrhoea include Salmonella, Shigella, Yersinia, E. coli, Pseudomonas, Clostridium dificile and sordelli, Stafylococcus aureus and Campylobactus. These pathogenic microorganisms adhere to the mucous membranes of the intestine and upset the intestinal function, thereby causing diarrhoea.

It is well-known that microorganisms affect each other positively or negatively by promoting or restraining each other's growth. This interference phenomenon has above all been studied in the flora of the skin, the pharynx and the intestine of human beings. Although the underlying causes are not fully known, it has been found that the normal bacterial flora is of considerable importance in the defence against pathogenic bacteria. The bacteria of the normal flora inhibit invading bacteria in many different ways, e.g. by producing antibiotic-like substances called bacteriocines. Unlike antibiotics, the bacteriocines mostly have a very selective effect on a specific group of bacteria without influencing the remaining bacterial flora. Treating infected patients with such harmless bacteria of specific effect has been not only discussed, but also tried to some extent. Naturally, the bacteria supplied must be able to settle in the intestinal area where they are to produce their effect. This is one of the ideas behind giving soured milk to patients whose intestinal flora is disturbed, and who suffer from severe diarrhoea after treatment with antibiotics. However, there has been no scientific follow-up of what actually happens with the intestinal flora, and the effect, if any, has mostly been uncertain, probably because no bacterial colonisation has taken place in the intestine or because the bacteria supplied lack the capacity to affect the diarrhoea-inducing bacteria. Efforts have also been made to replace the existing bacterial flora in the nasal mucous membrane, the skin and the pharynx with harmless microorganisms, and it has been shown that so-called recolonisation is possible and may be effective.

As mentioned above, supplying bacteria to patients suffering from different illnesses induced by pathogenic microorganisms has mostly been inconclusive, obviously because of insufficient knowledge of what bacteria strains are best suited for bringing about colonisation and interference.

By working under given conditions, it has in recent years been possible to establish important principles for the mechanisms controlling the interaction between different microorganisms, and also to develop methods for examining this interaction. Thus, it has become possible to intervene in this interaction in a meaningful and reproducible fashion, which may be used therapeutically/prophylactically when treating infections.

SUMMARY OF THE INVENTION

The present invention relates to a preparation for controlling pathogenic microorganisms in man and in animals, with a view to preventing and/or treating diarrhoea and other gastrointestinal troubles, said preparation being characterised by containing a viable microorganism strain in the form of Streptococcus lactis strain LIa in at least one pharmaceutically acceptable carrier medium in which the microorganism retains its viability. Further characteristics of the invention are apparent from the following text and the appended claims.

When studying the interaction between different bacteria, we have concentrated on the ability of certain lactic-acid bacteria to prevent the growth of pathogenic bacteria. On a laboratory scale, cultures of Streptococcus lactis have been tested, and a large number of clones with different biological properties have been isolated therefrom. Some of these have proved to have a pronounced inhibiting effect on most of the infection-inducing bacteria in man, such as Stafylococcus aureus, various species of Salmonella, Shigella, Pseudomas, Klebsiella-Entero, and Campylobactus.

An important reason for the effectiveness of the Streptococcus lactis strains is that some of these secrete bacteriocines which have a specific killing effect on some invading microorganisms.

The inventive pharmaceutical preparation has a microorganism strain content of $10^6$–$10^{10}$, preferably $10^8$–$10^9$, microorganisms/ml of final preparation ready for use.

In a preferred embodiment, the carrier for the microorganism strain is an acidulated or fermented milk product, such as soured milk, ropy milk, yoghourt, kefir and the like. The microorganism strain may be used as starter culture when preparing such milk products, which results in acidulated or fermented milk products having an increased content of the advantageous strain. Of course, it is also possible to add the bacteria to completed milk products, thereby obtaining a higher content in the medium of the desired bacteria. This embodiment is of considerable importance, since the preparation obtained is a wholesome and popular foodstuff. Such a preparation may be administered for prophylactic or curative purposes against diarrhoea and other intestinal infections often affecting infants. Further, it may be given to people who have received cancer therapy involving antibiotics or radiation, as well as to tourists travelling abroad where the bacterial flora is often different from that at home.

The preparation may also be in dry form for oral administration, e.g. as capsules, tablets or powder. The carrier media used in this case are of conventional type and well-known to the expert in the field. The capsules may be resistant to gastric juice, so that the bacteria are protected therefrom and only released in the intestine. For the same reason, tablets may be provided with a known coating which is resistant to gastric juice. Further, powders may be stirred prior to use in an aqueous liquid, such as water, milk and fruit juice.

The preparation has proved to be a highly effective prophylactic against various pathogenic intestinal bacteria causing gastrointestinal troubles, such as "tourist diarrhoea".

Advantageously, the preparation may also be used for treating Salmonella-infected people and animals.

Further, the preparation may also be adapted for treating animals, in which case the carrier is a suitable animal feed.

strain is typed or classified according to the API 20 system (API System, La Balme les Grottes, 38390 Montalieu, Vercieu, France).

TYPING TABLE
api 20 STREP

| TESTS | SUBSTRATES | REACTIONS/ENZYMES | RESULTS NEGATIVE | | RESULTS POSITIVE | |
|---|---|---|---|---|---|---|
| VP | Pyruvate | Formation of acetoin | colourless | | VP 1 + VP 2/wait for 10 min rose/red | |
| HIP | Hippurate | Hydrolysis | colourless/pale blue | | NIN/wait for 10 min dark blue/violet | |
| | | | 4 h | 24 h | 4 h | 24 h |
| ESC | Esculin | β-glycosidase | colourless pale yellow | colourless pale yellow light grey | grey black | black |
| | | | | ZYM A + ZYM B/10 min (1) decolour with intense light if need be | | |
| PYRA | Pyrrolidonyl-2-naphthyl amide | Pyrrolidonyl aryl amidase | colourless or very pale orange | | orange | |
| αGAL | 6-bromo-2-naphthyl-α-D-galactopyranoside | α-galactosidase | colourless | | violet | |
| βGUR | naphthol-AS-BI-β-D-glucuronate | β-glucuronidase | colourless | | blue | |
| βGAL | 2-naphthyl-β-D-galactopyranoside | β-galactosidase | colourless or very pale violet | | violet | |
| PAL | 2-naphthyl-phosphate | Alkaline phosphatase | colourless or very pale violet | | violet | |
| LAP | L-leucine-2-naphthyl amide | Leucine aryl amidase | colourless | | orange | |
| ADH | Arginine | Arginine dihydrolase | yellow | | red | |
| | | | 4 h | 24 h | 4 h | 24 h |
| RIB | Ribose | Acidulation | red | orange/red | orange/yellow | yellow |
| ARA | L-arabinose | Acidulation | red | orange/red | orange/yellow | yellow |
| MAN | Mannitol | Acidulation | red | orange/red | orange/yellow | yellow |
| SOR | Sorbitol | Acidulation | red | orange/red | orange/yellow | yellow |
| LAC | Lactose | Acidulation | red | orange/red | orange/yellow | yellow |
| TRE | Trehalose | Acidulation | red | orange/red | orange/yellow | yellow |
| INU | Inulin | Acidulation | red | orange/red | orange/yellow | yellow |
| RAF | Raffinose | Acidulation | red | orange/red | orange/yellow | yellow |
| AMD | Starch (2) | Acidulation | red | orange/red | orange/yellow | yellow |
| GLYG | Glycogen | Acidulation | red or orange | | light yellow | |

(1) At a second reading after 24 h of incubation, a precipitate may be noted in the tubes to which the reagents ZYM A and AYM B have been added. This is a normal phenomenon, which can be ignored.
(2) The acidulation of starch is often weaker than that of other sugars.

The microorganism should be kept in a freeze-dried state, preferably in skimmed milk in a dark and dry place, or frozen at a temperature of about −70° C.

The requisite dose of the inventive preparation is determined depending on such factors as the age and general state of the patient, as well as the type and seriousness of the illness. Anyone skilled in the art will have the competence necessary for determining the suitable dose. Another advantage of the invention is that a large overdose of the pharmaceutical preparation hardly involves any risks at all to the patient.

THE MICROORGANISM OF THE INVENTION

The microorganism strain forming part of the inventive pharmaceutical preparation was isolated in the following manner. A naturally-occurring *Streptococcus lactis* strain was isolated from a steepgrass, and examined for its inhibitory effect on pathogenic intestinal bacteria. Seven clones were tested, and one called LIa gave the best results.

This microorganism strain, which is used in the inventive preparation, was deposited in 1989 at The National Collection of Industrial and Marine Bacteria (NCIMB), Torry Research Station, P.O. Box 31, 135 Abbey Road, Aberdeen AB9 8DG, Great Britain. Its NCIMB accession number is 40157. The microorganism

| TEST WITH API 20 STREP | |
|---|---|
| VP | + |
| HIP | + |
| ESC | + |
| PYRA | − |
| αGAL | − |
| βGUR | − |
| βGAL | − |
| PAL | − |
| LAP | + |
| ADH | + |
| RIB | + |
| ARA | − |
| MAN | + |
| SOR | − |
| LAC | + |
| TRE | + |
| INV | − |
| RAF | − |
| AMD | − |
| GLYG | − |
| βHEM | − |

The strain has a weak α-hemolysis.
It grows well at 20°-37° C., and comparatively well at 39° C.
A suitable bouillon is M17, see recipe.
The strain belongs to the Lancefield N group.

MAKING SOURED MILK

In one embodiment of the invention, the pharmaceutically acceptable carrier medium for the preparation is soured milk.

When implementing this embodiment, the microorganism LIa according to the invention is allowed to grow in milk for 2-20 h, preferably 4 h. Then, the remaining soured-milk culture is added, which results in further growth, but at a reduced temperature of 21° C., if the temperature was higher at the beginning.

When the remaining soured-milk culture is added, the content of LIa should be $10^6$-$10^{10}$ cfu/ml, preferably $10^8$-$10^9$ cfu/ml. Then, the soured milk is left for 20-24 h, preferably 20 h, whereupon it is cooled and filled into containers.

After taking 260 ml of this soured milk in the morning and in the evening, the *Streptocuccus lactis* strain of the invention can be found in the intestine even after 3-5 days.

We claim:

1. A pharmaceutical composition for treating diarrhea cause by pathogenic gastrointestinal microorganisms comprising a viable microorganism strain of *Streptococcus lactis* strain LIa with NCIMB accession number 40157 in a pharmaceutically acceptable carrier.

2. The pharmaceutical composition of claim 1, wherein the microorganism strain content is $10^6$-$10^{10}$ microorganisms/ml.

3. The pharmaceutical composition of claim 2, wherein the microorganism strain content is $10^8$-$10^9$ microorganisms/ml.

4. The pharmaceutical composition of claim 1, wherein the pharmaceutically acceptable carrier medium is an acidulated or fermented milk product.

5. The pharmaceutical composition of claim 4, wherein the pharmaceutically acceptable carrier is an animal feed.

6. The pharmaceutical composition of claim 1, in a dry form.

7. A method of treating diarrhea caused by pathogenic gastrointestinal microorganisms in humans or animals comprising administering to a human or animal in need thereof an effective amount of a pharmaceutical composition comprising a viable microorganism strain of *Streptococcus lactis* strain LIa with NCIMB accession number 40157 in a pharmaceutically acceptable carrier.

8. The pharmaceutical composition of claim 4 wherein the acidulated or fermented milk product is soured milk, ropy milk, yoghurt or kefir.

9. The pharmaceutical composition of claim 6 wherein the dry form is a capsule, a tablet or a powder.

* * * * *

UNITED STATES PATENT AND TRADEMARK OFFICE
CERTIFICATE OF CORRECTION

PATENT NO. : 5,322,686

DATED : June 21, 1994

INVENTOR(S) : Eva E. Grahn; Stig E.F. Holm

It is certified that error appears in the above-identified patent and that said Letters Patent is hereby corrected as shown below:

Column 4, line 41, delete "AYMB" and insert therefor --ZYMB--.

Signed and Sealed this

Thirtieth Day of July, 1996

Attest:

BRUCE LEHMAN

Attesting Officer

Commissioner of Patents and Trademarks